United States Patent
Nacher et al.

(10) Patent No.: US 6,282,920 B1
(45) Date of Patent: Sep. 4, 2001

(54) APPARATUS AND METHOD FOR PRODUCING POLARIZED VAPOR-PHASE HELIUM-3, PARTICULARLY FOR NMR IMAGING

(75) Inventors: Jean-Pierre Nacher, Ivry sur Seine; Geneviève Tastevin, Paris, both of (FR)

(73) Assignee: Centre National de la Recherche Scientific-CNRS (FR)

( * ) Notice: Subject to any disclaimer, the term of this patent is extended or adjusted under 35 U.S.C. 154(b) by 0 days.

(21) Appl. No.: 09/134,788

(22) Filed: Aug. 14, 1998

(30) Foreign Application Priority Data

Feb. 16, 1996 (FR) .................................................. 96 01973
Feb. 6, 1997 (US) .................................... PCT/FR97/00240

(51) Int. Cl.[7] .......................................................... F25J 1/00
(52) U.S. Cl. ............................ 62/608; 62/51.2; 62/55.5; 62/919
(58) Field of Search ................................... 62/51.2, 55.5, 62/610, 919

(56) References Cited

U.S. PATENT DOCUMENTS 2,982,106 * 5/1961 Ambler .................................... 62/610
4,977,749 * 12/1990 Sercer .................................... 62/51.1
5,073,896 * 12/1991 Reid et al. .............................. 62/55.5

FOREIGN PATENT DOCUMENTS

| 0 471 586 | 2/1992 | (EP) . |
| 2 598 518 | 11/1987 | (FR) . |
| WO 91 07668 | 5/1991 | (WO) . |
| WO 95 27438 | 10/1995 | (WO) . |

* cited by examiner

*Primary Examiner*—Ronald Capossela
(74) *Attorney, Agent, or Firm*—Schnader Harrison Segal & Lewis LLP

(57) ABSTRACT

The present invention relates to an apparatus for producing polarized high-pressure vapor-phase helium-3, particularly for NMR imaging. The apparatus comprises a means for injecting helium-3 or a mixture of isotopes into an optical pumping cell (2), a means for liquefying the polarized gas from the optical pumping cell (2) and a tank (4) for storing the polarized liquid-phase helium-3, characterized in that the storage tank (4) is cooled to a temperature that may be set between a storage temperature Ta and an evaporation temperature Te, and communicates alternately with the optical pumping cell (2) and a high-pressure helium-3 gas discharge duct.

13 Claims, 1 Drawing Sheet

Figure 1:
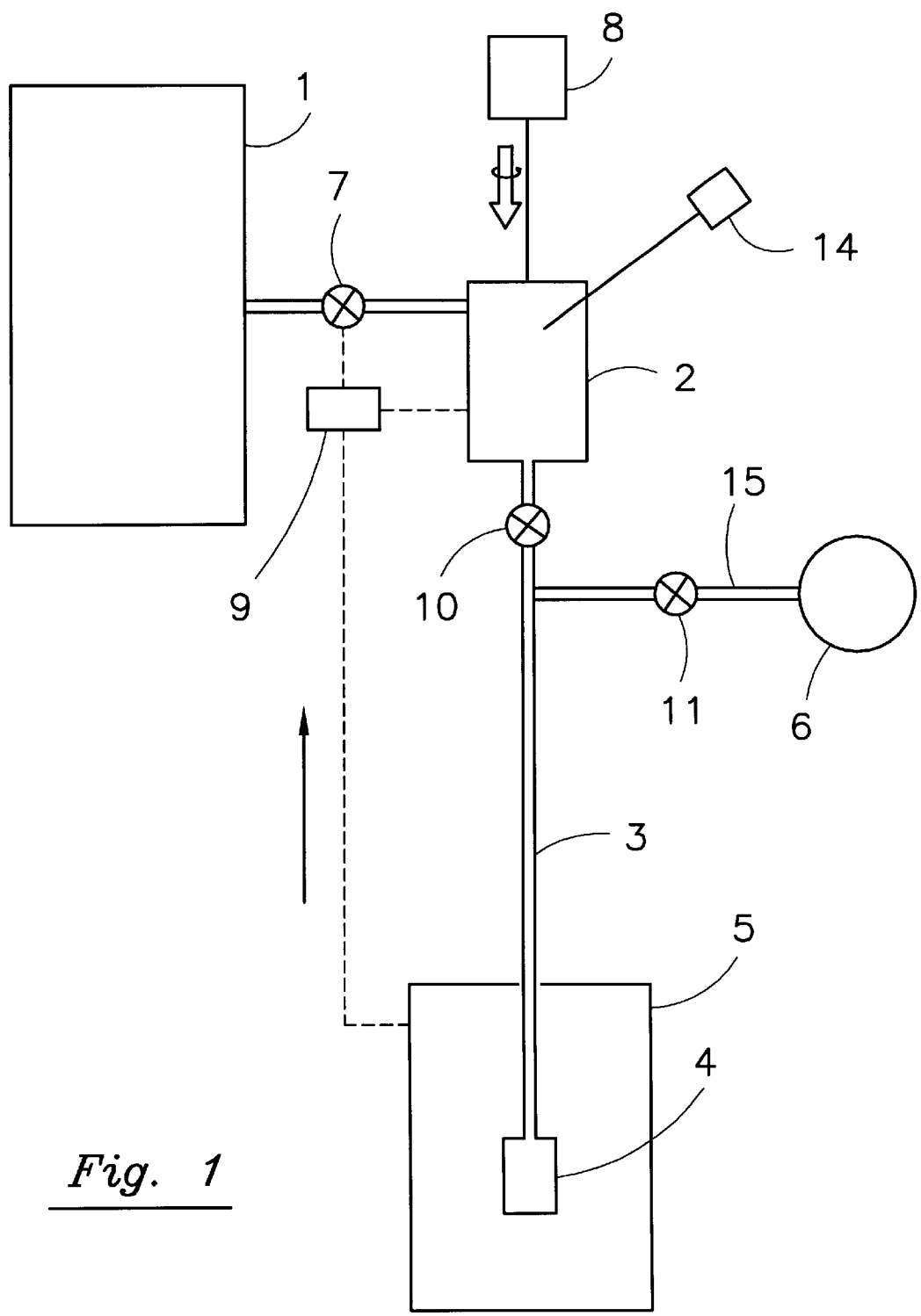

APPARATUS AND METHOD FOR PRODUCING POLARIZED VAPOR-PHASE HELIUM-3, PARTICULARLY FOR NMR IMAGING

The present invention relates to an apparatus and method for producing polarized high-pressure vapor-phase helium-3, particularly for NMR imaging, as well as the application of said apparatus.

Polarized helium-3 is an isotope known for the properties which have been exploited particularly for the measurement of extremely small variations in the terrestrial magnetic field, particularly for the fabrication of magnetometers. The state-of-the-art methods for producing dense polarized helium-3 are relatively difficult to implement. A first method, referred to as the "brute-force" method, is comprised of placing a helium-3 sample in an intense magnetic field at low temperature. This method is only effective for solid helium-3 at a pressure greater than 36 atmospheres or for helium-3 that is highly diluted in liquid helium-4, at a temperature of several millikelvin in a magnetic field of several teslas. These conditions pose noteworthy technological problems and prevent production under conditions that are economically acceptable for applications requiring production within a reasonably short period of time of large volumes of polarized helium-3.

Also proposed in the prior art has been polarization by spin exchange with a gas of alkaline atoms oriented by optical pumping. This method is also very slow because the exchange collisions that assure the transfer of polarization from the alkaline to the helium are of low efficacy and constitute an insurmountable limiting factor. This method requires a duration of 10 hours for the polarization of 150 cubic centimeters of helium at a pressure of 10 bars and a polarization of 10%.

Another method of the prior art, which constitutes the state of the art that is closest to the invention, comprises compressing gaseous helium-3 polarized by optical pumping using a mobile-piston compressor. This type of device is very delicate to fabricate and operate. Extremely rigorous precautions need to be taken to avoid relaxation during the compression phase, upon passage into the pump. Specifically, it is necessary to avoid use of lubricants that could contaminate the polarized gas and to select materials for the pump walls such that they reduce the relaxation of the polarized isotopes. This method can be implemented for research applications in laboratories but it can not be used at present for producing under economically acceptable conditions noteworthy quantities of strongly polarized helium-3 within brief time periods.

The object of the present invention is to resolve the drawbacks of the methods and apparatus of the prior art by proposing a method enabling the rapid production of highly polarized helium-3 in the form of dense gas, at a pressure on the order of atmospheric pressure or higher than atmospheric pressure, using a low-cost apparatus with uncomplicated operations.

To this end, the invention relates first of all to an apparatus for producing polarized high-pressure vapor-phase helium-3, particularly for NMR imaging. The apparatus comprises a means for injecting helium into an optical pumping cell, a means for liquefying the polarized gas from the optical pumping cell and a tank for storing the polarized liquid-phase helium-3, characterized in that the storage tank is cooled to a temperature that can be set between a storage temperature Ta and an evaporation temperature Te, and communicates alternately with the optical pumping cell and with a high-pressure gas-phase helium discharge duct.

The apparatus according to the invention operates according to a purely cryogenic compression principle, and employs solely the thermal effects for displacing the atoms. It is thus possible to avoid in particular all of the problems stemming from the use of a pump for the compression of the polarized gas.

Preferably, the optical pumping cell communicates with the helium-3 source via an adjustable-flow valve. In comparison with the spin-exchange method with optically polarized alkaline atoms, the major advantage is the rapidity of the production of the orientation by means of direct optical pumping of the helium.

According to a preferred mode of implementation, the optical pumping cell has a means for determining the nuclear polarization of the gas.

This means, for example a device for measuring the polarization of the florescence radiation emitted by the gaseous mixture in the optical pumping cell, enables control of the polarization rate of the gaseous mixture in the pumping cell and the adjustment of certain settings of the apparatus so as to maximize this rate. To this end, the apparatus has means for setting the flow rate of the pumping cell's feed valve and/or the temperature Ta of the storage tank as a function of the nuclear polarization in the optical pumping cell (indicated by dotted lines in the figure.

According to a preferred mode of implementation, the optical pumping cell is excited by a laser emitting a beam with a wavelength of 1083 nanometers.

For example, a laser diode with a power of 50 milliwatts enables preparation of 100 cubic centimeters of a mixture containing 10% of helium-3 under a pressure of 1.2 bar in 15 minutes.

The invention also relates to a method for producing polarized vapor-phase helium-3 comprising the injection of helium-3 into an optical pumping cell and the storage of the polarized helium-3 in liquid phase in a storage tank, characterized in that the polarized gas from the optical pumping cell is collected in a storage chamber cooled to a temperature that can be set between a helium-3 liquefaction temperature Ta and a helium-3 evaporation temperature Te.

Advantageously, a mixture of helium-3 and helium-4 is injected into the optical pumping cell. It has been found that the use of a mixture rather than pure helium-3 results in the lengthening of the time period during which the polarization can be maintained. Said mixture preferably contains between 3 and 30% of helium-3.

According to an advantageous variant, part of the polarized helium contained in the storage tank is evaporated. This variant is manifested by an enrichment in polarized helium-3 in the polarized gaseous mixture produced by the apparatus. In addition, use can be made of enrichment techniques that employ the thermodynamic effects characteristic of superfluid helium.

The invention also relates to the application of an apparatus in accordance with the preceding to NMR imaging. The body to analyze is penetrated by a polarized gaseous mixture stemming from an apparatus according to the invention and NMR imaging of said body is performed.

Enhanced comprehension of the invention will be provided by the description below of a nonlimitative example of implementation with reference to the attached drawings in which:

FIG. 1 represents a schematic view of the apparatus;

FIG. 1 represents a schematic view of an apparatus according to the invention. It is constituted by a tank (1) containing a gaseous mixture of helium-3 and helium-4. The mixture contains a proportion of circa 10% helium-3 for 90% helium-4.

A valve (7) enables injection of the mixture into an optical pumping cell (2). This valve (7) can also be used to act on the injection flow rate of the mixture into the cell (2).

The pumping cell (2) is a volume allowing circulation of the atoms between the tank (1) and a duct (3) opening into a storage tank (4). The cell (2) is made of a nonrelaxant transparent material such as glass, and is positioned on the path of a laser beam with a wavelength of 1083 nanometers. A polarimeter (9) allows analysis of the fluorescence light emitted by the mixture contained in the cell (2) and calculation from that of the nuclear polarization rate. This measurement can be used to monitor the efficacy of the optical pumping. As a variant, it is possible to directly measure the magnetization of the gas in the cell (2) by NMR, magnetometry, etc.

The outlet of the cell (2) empties into a storage chamber (4) that has walls made of a nonrelaxant material. This storage chamber (4) is cooled by a cooling system (5) allowing the temperature to be set so as to condense or evaporate the $^3$He—$^4$He mixture contained in the storage chamber (4). The cooling system can be, for example, a pumped helium-4 refrigerator. This type of device makes it possible to reach temperatures on the order of 0.9 K.

During the accumulation phase, the temperature of the chamber (4) must be below 1.8 K so that all vapor pressure concentrations remain below 10 torr in order to allow optical pumping. The temperature of the chamber (4) determines directly the pressure within the optical pumping cell (2) and thus the efficacy of the optical pumping. It is thus possible to maximize the polarization rate by acting either on the temperature of the storage chamber (4) or on the mixture injection flow rate via the valve (7). The gas flow rate into the optical pumping cell (2) must be adjusted to the luminous flux available for polarizing the helium-3 atoms. It thus determines the refrigeration power required for liquefaction. The correspondence scale for these three quantities is the following:

1 W of laser power from laser (14) enables correct polarization of up to $10^{18}$ helium-3 atoms per second, which corresponds to circa 0.75 liters per second of a 4% gas mixture under one torr, which produces 1.3 mm$^3$ per second of 4% liquid mixture. Liquefaction of the mixture at this rate releases a latent heat of 4 millijoules per second, an output which can be easily handled by the refrigeration system. The time subsequently required for evaporation of the accumulated liquid is negligible if a heating power greatly superior to 4 mW is employed. In the final assessment, the polarized dense gas production rate is limited only by the laser power to 1 bar·cm$^3$/s for 1 watt.

It is also possible to control the temperature of the storage chamber (4) and/or the mixture injection rate by means of the measurement of the polarization rate delivered by the device (9).

During the evaporation phase, a slight temperature elevation is provided, for example by calorific input from a small heating resistance, and a first valve (10) is closed so as to isolate the optical pumping cell (2) and a second valve (11) is opened so as enable injection of the polarized mixture into a storage volume (6) of gas under high pressure or directly into a connector linked to the injection apparatus into a hollow body or via inhalation by a patient via discharge duct (15).

As an example, the table below shows the vapor pressure (in torr) for various temperatures and concentrations of helium-3:

|         | 3%   | 10% | 30% |
|---------|------|-----|-----|
| T = 0.9K | 0.82 | 2.1 | 3.6 |
| T = 1.1K | 1.8  | 4.5 | 8.3 |
| T = 1.3K | 3.7  | 8.4 | /   |

During the evaporation phase, the pressure increases with the temperature T of the volume (4). For a final pressure of 1 bar, T is on the order of 4 K for concentrations of several percents. The critical pressure beyond which there is no longer any possible liquid/vapor equilibrium is on the order of 2.3 bar for helium-4. Beyond that point, the heat dilates the fluid and further increases the pressure as shown in FIG. 2.

A first mode of utilization is comprised of evaporating totally the liquid accumulated in the tank (4) and heating it sufficiently and liberating from it the totality of the resultant polarized gas.

A second mode of utilization is comprised of evaporating only partially the accumulated liquid. Since the helium-3 is more volatile, its concentration in the vapor is greater than that of the liquid. The gas recovered under high pressure is thus richer in helium-3 than in the initially condensed mixture. The residual liquid remaining in the tank (4) will, obviously, contain a larger proportion of helium-4.

A third mode of utilization is comprised of first extracting from the solution contained in the tank (4) a noteworthy fraction of the helium-4 and then performing the evaporation of resultant enriched liquid. Various thermomechanical effects characteristic of superfluid helium can be used to isolate the helium-4: passage of a superleak, heat-flush effect, hevac effect.

The entire volume accessible to the polarized fluid should be subjected to a magnetic field that is sufficiently homogenous so as not to induce relaxation. Its amplitude is determined by the quality of the ambient magnetic environment: in general, one millitesla is sufficient. The amplitude should not exceed several tens of milliteslas in order for the optical pumping to remain effective.

One cubic centimeter of liquid helium evaporated at ambient temperature produces 745 cubic centimeters of gas at atmospheric pressure. Thus, for example, 4 cm$^3$ of solution accumulated in the chamber (4) will yield one liter of gas at 3 bar. If only one third of this liquid is evaporated, and its initial concentration was 3%, one liter of gas will be recovered at one bar with a concentration of 5.8%.

A first application relates to NMR imaging of hollow body cavities, for example the lungs, of a patient or an animal. It is advisable to implement inhalation of a gaseous mixture containing polarized helium-3 prepared with an apparatus such as previously described.

A second application is the imaging of organic or biological fluids or tissues in which polarized helium-3 has been diffused.

A third application is the characterization of porous materials or bodies by NMR measurement using polarized helium-3 as a local probe.

The invention is described above as nonlimitative examples.

What is claimed is:

1. Apparatus for producing polarized vapor-phase helium-3, particularly for NMR imaging, with the apparatus comprising a means for injecting helium-3 or a mixture of isotopes into an optical pumping cell (2) for polarizing said helium-3, a means for liquefaction of the polarized gas from the optical pumping cell (2) and a tank (4) for storing the polarized helium-3 in liquid phase, wherein the tank (4) is selectively temperature controlled, for establishing phase and pressure as a function of temperature, between a storage temperature Ta and an evaporation temperature Te, and including means for alternatively communicating said tank (4) with said optical pumping cell (2) and with a high-pressure helium-3 gas discharge duct through which vapor-phase helium-3, generated by evaporation within said tank is discharged.

2. Apparatus for producing polarized vapor-phase helium-3 according to claim 1, wherein the optical pumping cell (2) communicates with the source of helium-3 via an adjustable-flow valve (7).

3. Apparatus for producing polarized vapor-phase helium-3 according to claim 1 or 2, wherein the optical pumping cell (2) includes a nuclear polarization determination means.

4. Apparatus for producing polarized vapor-phase helium-3 according to claim 1 further comprising means for adjusting the flow rate of the pumping cell inlet valve and/or of the storage temperature Ta of the tank (4) in relation to the nuclear polarization in the optical pumping cell (2).

5. Apparatus for producing polarized vapor-phase helium-3 according to claim 1, further comprising means to enable total or partial evaporation of the polarized liquid accumulated in the tank (4) in the form of a high-pressure gas.

6. Apparatus for producing polarized vapor-phase helium-3 according to claim 1, wherein the optical pumping cell (2) is excited by a laser emitting a beam with a wave length of 1083 nanometers.

7. Method for producing polarized vapor-phase helium-3 comprised of injecting helium-3 into an optical pumping cell (2), polarizing helium-3 in said optical pumping cell; and collecting and storing the polarized helium-3 in liquid phase in a storage tank, that is selectively temperature controlled between a helium storage temperature Ta and a helium evaporation temperature Te; and evaporating and discharging at least a portion of said stored liquid polarized helium-3 to produce vapor phase polarized helium-3.

8. Method for producing helium-3 according to claim 7, wherein a mixture of helium-3 and helium-4 is injected into the optical pumping cell (2).

9. Method for producing helium-3 according to claim 8, wherein said mixture contains between 3 and 30% of helium-3.

10. Method for producing helium-3 according to one of claims 7 to 9, wherein the flow rate and/or the temperature of the cooled tank (4) is adjusted in relation to the nuclear polarization measured in the optical pumping cell (2).

11. Method for producing helium-3 according to claim 7 further comprising the steps of:
   supplying a calorific increase to said storage tank to raise its temperature to an evaporation temperature Te;
   evaporating collected, liquified helium-3 as a result of said calorific increase; and
   delivering the resultant vapor-phase polarized helium-3.

12. Method for producing helium-3 according to claim 7, wherein said evaporation of part of the polarized liquid contained in the tank (4) is to enrich the helium-3 rate delivered by the apparatus.

13. Body imaging method comprising the steps of storing polarized helium-3 in a tank (4) that is selectively temperature controlled between a storage temperature Ta and an evaporation temperature Te, with said tank communicating alternately with an optical pumping cell (2) and with a helium-3 gas discharge duct; discharging vapor phase, polarized helium-3 through said duct; and penetrating said body with said vapor phase, polarized helium-3.

* * * * *